(12) United States Patent
Jijakli et al.

(10) Patent No.: US 7,241,439 B2
(45) Date of Patent: Jul. 10, 2007

(54) BIOPESTICIDE COMPOSITIONS

(75) Inventors: Mohamed Haïssam Jijakli, Brussels (BE); Philippe Berto, Vernon (FR); Catherine Dickburt, Villers-la-Ville (BE); Philippe Lepoivre, Grand Leez (BE)

(73) Assignee: Faculte Universitaire des Sciences Agronomiques de Gembloux, Gembloux (BE)

( * ) Notice: Subject to any disclaimer, the term of this patent is extended or adjusted under 35 U.S.C. 154(b) by 261 days.

(21) Appl. No.: 10/471,144

(22) PCT Filed: Mar. 1, 2002

(86) PCT No.: PCT/EP02/02224

§ 371 (c)(1),
(2), (4) Date: Oct. 14, 2003

(87) PCT Pub. No.: WO02/069720

PCT Pub. Date: Sep. 12, 2002

(65) Prior Publication Data

US 2004/0096428 A1   May 20, 2004

(30) Foreign Application Priority Data

Mar. 5, 2001 (EP) ................... 01200812

(51) Int. Cl.
| | | |
|---|---|---|
| *A01N 63/00* | (2006.01) | |
| *A01N 65/00* | (2006.01) | |
| *A01N 59/06* | (2006.01) | |
| *A01N 59/08* | (2006.01) | |
| A61K 33/42 | (2006.01) | |
| A61K 33/00 | (2006.01) | |
| A61K 33/14 | (2006.01) | |
| A61K 33/10 | (2006.01) | |

(52) U.S. Cl. .................... 424/93.1; 424/93.4; 424/602; 424/611; 424/678

(58) Field of Classification Search .................. 514/54; 424/93.1, 93.2, 93.3, 93.4, 93.5, 93.51, 93.6, 424/602, 610, 611, 678, 686

See application file for complete search history.

(56) References Cited

U.S. PATENT DOCUMENTS

| | | | | |
|---|---|---|---|---|
| 4,950,472 A | * | 8/1990 | Janisiewicz ................ 424/93.5 |
| 5,288,488 A | * | 2/1994 | Backman et al. .......... 424/93.4 |
| 5,413,783 A | * | 5/1995 | McLaughlin et al. .... 424/93.51 |
| 5,588,254 A | * | 12/1996 | Adachi et al. ............... 47/57.6 |

OTHER PUBLICATIONS

Sawant et al. Applied and Environmental Microbiology 1988, 54(5), 1099-1103.*
Marquina et al. Int Microbiol. 2002, 5, 65-71.*
Data from CBS Fungi database Jan. 20, 2006.*
Abstract: Dickburt et al. Phytopathology Jun. 2001, 91(6), supplement p. S23.*

* cited by examiner

*Primary Examiner*—Johann Richter
*Assistant Examiner*—Ernst Arnold
(74) *Attorney, Agent, or Firm*—Knobbe, Martens, Olson & Bear, LLP

(57) ABSTRACT

The present invention relates to compositions suitable for use against one or more pathogens comprising at least one antagonistic micro-organism and at least one stimulating agent, which may be selected from the group consisting of one or more uronic acids, mannans, and/or derivatives thereof and mixtures of said agents. The invention also relates to a method for the biocontrol of disease caused by pathogens to vegetal material using the compositions of the invention.

10 Claims, No Drawings

BIOPESTICIDE COMPOSITIONS

RELATED APPLICATIONS

This application is the U.S. National Phase under 35 U.S.C. § 371 of International Application PCT/EP02/02224, filed Mar. 1, 2002, which was published in English and which claims priority of EP 01200812.4, filed Mar. 5, 2001 Each of the above applications are incorporated herein by reference in their entirety.

FIELD OF THE INVENTION

The present invention relates to biopesticide compositions containing antagonistic microorganisms and stimulating agents. Said compositions have an improved and/or longer efficacy against diseases caused by pathogens to vegetal material, for instance diseases caused by moulds that colonise parts of plants, either after harvesting or during the plant life cycle, such as *Penicillium* or *Botrytis* spp.

BACKGROUND OF THE INVENTION

A great number of pesticides is well known in the art and has intensively been used for many years. There is presently a tendency to contemplate the possibility of using alternative methods involving more environment-friendly products.

It is well known in the art to use, as biological control agents, micro-organisms that are antagonistic to plant pathogens. Such micro-organisms can be effective biocontrol agents for the biological control of plant diseases, in particular postharvest diseases.

*Penicillium* and *Botrytis* species are responsible for important economical losses. *Botrytis* may cause important damages to plants for instance in the production of tomato, grapevine and strawberry prior to harvesting, and postharvest diseases on *Malus* and *Pyrus* spp. The common occurrence of *Penicillium* species in food is a particular problem. Some species produce toxins and may render food inedible or even dangerous. Species of *Penicillium* can cause severe fruit rot for example on *Malus, Pyrus* and *Citrus* spp.

STATE OF THE ART

Biocontrol of plant diseases is well known in the art. Patent documents which relate to the use of compositions comprising yeast's or other micro-organisms against plant pathogens have been published, amongst which WO99/62340, WO99/62341, U.S. Pat. No. 5,525,132, USA-5,741, 699, U.S. Pat. No. 5,288,488 and U.S. Pat. No. 5,780,023 may be cited as examples.

Various micro-organisms amongst bacteria, fungi and yeast's have successfully been used against plant diseases caused by pathogens.

According to a 1998 publication from S. Frey and N. Magan, the Applied Microbiolgy group, Biotechnology Centre, Cranfield University and entitled "Ecophysiology, Growth and spore germination of *Ulocladium atrum*, a biological control agent of *Botrytis cinerea*" (7th International Congress of Plant Pathology), the fungus *U. atrum* has been shown to be a very effective biocontrol agent against *B. cinerea* in the phyllosphere of a number of crops by preemptive exclusion of the pathogen and suppression of the sporulation.

Numerous yeast strains exhibiting antagonism against *Botrytis* and/or *Penicillium* spp. have been reported in the literature and some yeast strains have shown interesting protective properties.

Commercial biocontrol products such as Biosave™ (*Pseudomonas syringae* van Hall, Esc-11) and Aspire™ (*Candida oleophila* Montrocher, 1-182) are already available respectively from Ecoscience Corp. (Worcester, Mass.) and Ecogen Inc. (Longhorn, Pa.) and are used among others on postharvest apples against wound diseases.

However, these first generation biocontrol products, relying on the use of single antagonists, have been criticised for not providing a stable and reliable protective activity when used under commercial conditions. The protection against pathogens that the prior art provides at ambient temperature does usually not exceed one week under severe conditions of infection.

The present inventors isolated amongst 329 epiphytic micro-organisms two yeast's strains, disclosed for the first time in Jijakli, M. H and Lepoivre P. 1993, *Biological control of postharvest Botrytis cinerea and Penicillium on apples,* IOBC/WPRS Bulletin: *Biological Control of Foliar and Postharvest diseases* 16, pp. 106-110, which have proved themselves particularly efficient against diseases caused by *Botrytis* and *Penicillium* spp. on apples and pears.

These strains were both isolated from the surface of apples. Strain K has been deposited under number 40563 at the BBCM™/MUCL Culture Collection of the Mycothèque de l'Université Catholique de Louvain has been identified as *Pichia anomala* (Hansen) Kurtzman. Strain O has been deposited under number 40564 at the BBCM™/MUCL Culture Collection of the Mycothèque de l'Université Catholique de Louvain. Strain O was first supposed to be a strain of Candida sake. Further analyses seemed to indicate that it belonged to *Debaryomyces hansenii* var. *hansenii*; however, strain O finally revealed to be a strain of *C. oleophila* Montrocher. The geographical origin and the molecular profile (revealed by RAPD technique) of strain O are quite different from the above-mentioned strain I-182 commercialised under the name Aspire™.

The interest for biological control over chemical control is rapidly growing for some reasons, such as environmental concerns, apparition of pathogen strains resistant to chemical pesticides or limitation of use of chemical pesticides.

Although promising results have been obtained until now, there is a strong need to improve efficiency of biopesticide compositions.

It is desired to lower the utilisation costs by using more efficient compositions enabling to use lesser quantities of antagonistic micro-organisms per treatment, without lowering the efficiency of the composition against pathogens and without restricting the duration of the efficiency of the composition against pathogens, and to reach the economical threshold of profitability.

AIMS OF THE INVENTION

The invention aims to provide novel compositions containing antagonistic microorganisms, which are suitable for use against diseases caused to vegetal materials by pathogens, especially diseases induced by moulds, and a new method for the biocontrol of diseases such compositions, caused by pathogens to vegetal material using such compositions.

Another aim of the invention is to provide such compositions that are at least as efficient as the ones of the state of the art.

The invention also aims to provide such compositions, which comprise lower concentrations of antagonistic microorganisms while having a similar efficiency against the pathogens.

A further aim of the invention is to provide such compositions, which comprise lower concentrations of antagonistic micro-organisms while prolonging the duration of the efficiency of the compositions against the pathogens.

SUMMARY OF THE INVENTION

By "stimulating agent", is meant, according to the present invention, an agent which is liable to stimulate biological properties of a micro-organism. For example, it may stimulate the biological properties of antagonistic micro-organisms against pathogens able to cause diseases to vegetal material.

By "antagonistic micro-organism" is meant, according to the present invention, a micro-organism which is an antagonist to a pathogen, in particular a pathogen which is liable to cause diseases to vegetal material.

The invention relates to a composition suitable for use against one or more pathogens comprising at least one antagonistic micro-organism and at least one stimulating agent chosen from the group consisting of one or more uronic acids, mannans and/or derivatives thereof, and mixtures of said agents. By "derivatives" is meant chemical derivatives, such as for instance salts and hydrates and the like.

In a preferred embodiment, the invention relates to a composition further comprising a beta-1,3-glucan.

Preferably, uronic acids are chosen from the group consisting of galacturonic acid and glucuronic acid. The preferred amount of the at least one stimulating agent is comprised between 0.001 and 0.2% w/v.

According to a preferred embodiment of the invention, said at least one antagonistic micro-organism is selected from the group consisting of fungus and yeast. Said fungus is advantageously a *U. atrum* strain (hereinafter designated as *U. atrum* 385).

This strain 385 which corresponds to a strain deposited by Plant Research International, formerly Research Institute for Plant Protection (Wageningen) (IPO-DLO) at CBS (Centraalbureau voor Schimmelcultures, Upsalalaan 8, NL—3584 CT Utrecht, The Netherlands) under number 700.95.

Said yeast is advantageously chosen from the group consisting of *Pichia anomala* and *Candida oleophila*.

In a particularly preferred embodiment of the invention, the yeast is under the form of a strain selected from the group consisting of *Pichia anomala* (Hansen) Kurtzman strain K deposited under MUCL-40563, *Candida oleophila* Montrocher strain O deposited under MUCL-40564, both deposited on Jun. 17, 1997 at the BBCM™/MUCL Culture Collection of the Mycothèque de l'Université Catholique de Louvain, Place Croix Du sud 2-bte. 6, B1348Louvain-la-Newve, Belgium, and *Candida oleophila* Montrocher commercial strain I-182.

Said antagonistic micro-organism is preferably applied at a concentration ranging from $10^5$ to $10^8$ cfu/ml.

One or more pathogens are able to cause diseases to vegetal material. The latter may be selected from the group consisting of fruits particularly the species *Malus* spp., *Pyrus* spp., *Citrus spp.*, of crops particularly from the species tomato, grapevine and strawberry, and of flowers and other ornamental crops.

The pathogens may be selected from the group consisting of *Botrytis cinerea, Penicillium expansum, P. digitatum, P. italicum , Rhizopus* spp.

The compositions of the invention may further comprise at least one salt chosen amongst calcium salt, sodium salt, and potassium salt, amongst which the calcium salt is selected from the group consisting of calcium chloride, calcium bicarbonate and calcium propionate. The amount of salts may be in the range of 0.01% and 2% w/v.

The invention also relates to a method for the biocontrol of diseases caused by pathogens to vegetal material, comprising the step of applying a composition according to the invention to said vegetal material.

It also relates to the use of a composition according to the invention as a biopesticide, and to a method for the manufacture of a biopesticide comprising a composition according to the invention.

Furthermore, the invention also relates to the use of a stimulating agent according to the invention to stimulate biological properties of a micro-organism, in particular in a biopesticide composition.

The invention also relates to the use of a stimulating agent for lowering the concentration of an antagonistic micro-organism without lowering the efficiency of the composition against pathogens, and to the use of a stimulating agent for lowering the concentration of an antagonistic micro-organism while prolonging the duration of the efficiency of the composition against pathogens.

The invention also relates to a method for stimulating the biological properties of a micro-organism in a biopesticide composition comprising adding a stimulating agent to said biopesticide composition.

In said method, stimulating the biological properties of the micro-organism may comprise lowering the concentration of an antagonistic micro-organism without lowering the efficiency of the composition against pathogens. Stimulating biological properties may also comprise lowering the concentration of an antagonistic micro-organism while prolonging the duration of the efficiency of the composition against pathogens.

EXAMPLES

The invention will be further illustrated below by the description of some ways of carrying it out.

Example 1

Example 1 illustrates the fact that good protective effect may be obtained by using compositions of the invention comprising stimulating agents consisting of uronic acids and antagonistic yeast's active against postharvest diseases caused by moulds on fruits of *Malus* species.

Vegetal Material

Apples (*Malus domestics* Borkh cv. Golden) were harvested from commercial orchards maintained with standard cultural practices in Belgium and placed in regular long term storage. Commercial class I fruits were used. They were bought from wholesale dealers and stored in a cold room at 4±1° C. for maximum 15 days before use.

Pathogens

*B. cinerea* (grey mould) and *Penicillium* expansum (blue mould) strains were initially isolated from strawberries and apples respectively in Gembloux.

Conidia from the two pathogenic strains were put in suspension in a glycerol solution (25%) and stored at −70° C. Another storage method consisted of growing the pathogen on Potato Dextrose Agar (PDA) in tubes, covering it then by paraffin oil and keeping the tubes at 25° C. Starting from this stored material, the two fungal strains were transferred to oat medium at 25° C. Conidial suspensions were prepared in an aqueous sterile solution of Tween 20 (0.05%), and were adjusted to the required concentration ($10^6$ spores/ml) using a Bärker cell.

Antagonistic Micro-Organisms

The antagonistic yeast strains

*Pichia anomala* (Hansen) Kurtzman deposited under number 40563 at the BBCM™/MUCL Culture Collection of the Mycothèque de l'Université Catholique de Louvain, hereinafter designated as "strain K", and

*Candida oleophila* Montrocher deposited under number 40564 at the BBCM™/MUCL Culture Collection of the Mycothèque de l'Université Catholique de Louvain, hereinafter designated as "strain O"

have been isolated from apple surface and stored at −70° C. in a glycerol solution (25%) or under paraffin oil on PDA in tubes kept at 25° C.

Before use, the micro-organisms were subcultured three times successively at 24 hours intervals on PDA (Potato Dextrose Agar). At the third generation, yeast cells were removed from the culture medium and suspended in isotonic water (NaCl 0.85%). Suspension concentrations were adjusted to the required values after the establishment of a regression line in relation with the micro-organisms suspension absorbance (at 595 nm) and the number of colony forming units (cfu) of the same suspension spread onto PDA.

Treatment

Fruits were disinfected by dipping for 2 minutes in sodium hypochlorite (10% of the commercial product). They were rinsed in sterile water and dried out under laminar flux before being wounded by removing 6 mm diameter and 3 mm deep blocks of tissue from two sites 4-5 cm apart along the equatorial line of the fruits.

The wounds were treated by application of 50 µl of compositions of the state of the art or compositions of the invention.

After a 24 h at 20° C. incubation period in plastic boxes, the wounds have been inoculated with 50 µl of the respective conidial suspensions of the pathogens. The fruits were incubated during one to three weeks at 25° C.

The diameters of the lesions developing around the wounds were measured after 7, 10, 14 and up to 20 days after treatment. Four fruits (8 wounds) were used per treatment.

The percentage of protection provided by the different treatments is calculated from the diameter of lesion caused by the fruit rot agent after the incubation time using the following formula:

$$\frac{D_T - D_X}{D_T} \times 100 = Y\%$$

where Y is the percentage of protection; $D_T$ is the mean diameter of lesions for the untreated control and $D_X$ is the mean diameter of lesions for the treated fruits.

The effect of the compositions of the invention against postharvest apple rots caused by the pathogens (*B. cinerea*, respectively *P. expansum*) has been evaluated under controlled conditions.

In the remaining parts of this text, GA stands for galacturonic acid (monohydrate) 98%, Sigma G2125, PGA stands for polygalacturonic acid 95% Fluka 81325 whereas GU stands for glucuronic acid (sodium salt), Sigma G8645. These products are known per se and commercially available.

TABLE 1

| Strain K (cfu/ml) | GA (% w/v) | GU (% w/v) | % protection against *B. cinerea* after | | | |
|---|---|---|---|---|---|---|
| | | | 7 days | 10 days | 14 days | 20 days |
| $10^7$ | — | — | 98 | 94 | 72 | 36 |
| $10^5$ | — | — | 94 | 73 | 57 | 27 |
| — | 0.01 | — | 49 | 42 | 22 | 2 |
| — | — | 0.001 | 75 | 46 | 46 | 21 |
| $10^5$ | 0.01 | — | 100 | 100 | 65 | 29 |
| $10^5$ | — | 0.001 | 100 | 100 | 94 | 66 |

In a first series of experiments, standard compositions of strain K have been used as control. The standard rate for the use of strain K is $10^7$ colony forming units per millilitre (cfu/ml), whereas the rate of $10^5$ cfu/ml is considered as suboptimal. Indeed, it can be seen in table 1 that results (which are expressed in terms of percentage of protection calculated as defined above), obtained with this rate when using strain K alone are not satisfactory.

It has surprisingly been found that, according to the invention, a significant effect on the protection against *B. cinerea* is obtained when using respectively 0.01% w/v GA and 0.001% w/v GU.

Furthermore, according to the invention, it has surprisingly been found that a composition that comprises the suboptimal rate of $10^5$ cfu/ml of strain K and galacturonic acid monohydrate (GA) 0.01% w/v nevertheless allows a total protection (100%) even after 10 days.

Similarly, it has been surprisingly found that a composition which comprises the suboptimal rate $10^5$ cfu/ml of strain K and GU 0.001% w/v also allows a total protection (100%) even after 10 days. This composition further allows a percentage of protection exceptionally high after 14 days. Even after 20 days, the percentage of protection obtained by using this composition is impressively higher than the percentages provided by compositions of the state of the art.

It appears that, according to the invention, the addition of GA or GU allows to reduce the rate of strain K hundred fold (down to $10^5$ cfu/ml) while obtaining a better efficacy against *B. cinerea* than with the standard rate of compositions of the state of the art. This result is remarkable.

In a second series of experiments on apples, results of which are given in table 2, standard compositions of strain O have been used as control.

TABLE 2

| Strain O (cfu/ml) | GA (% w/v) | GU (% w/v) | % protection against *B. cinerea* after | | | |
|---|---|---|---|---|---|---|
| | | | 7 days | 10 days | 14 days | 20 days |
| $10^7$ | — | — | 100 | 82 | 84 | 74 |
| $10^5$ | — | — | 69 | 75 | 65 | 40 |
| — | 0.001 | — | 87 | 47 | 33 | 0 |
| — | — | 0.001 | 75 | 46 | 46 | 21 |
| $10^5$ | 0.001 | — | 100 | 90 | 84 | 66 |
| $10^5$ | — | 0.001 | 100 | 100 | 90 | 53 |

In the first composition, the rate of strain O is the standard rate of $10^7$ cfu/ml, whereas in the second one, the rate is the suboptimal rate of $10^5$ cfu/ml.

Here again, it has surprisingly been found that, according to the invention, a significant effect on the protection against B. cinerea is obtained when using respectively GA 0.001% w/v and GU 0.001% w/v. In both cases, it is worth noting that the result obtained is even better than the ones obtained with the compositions containing only strain O at $10^5$ cfu/ml.

Moreover, GA 0.001% w/v has a greater efficacy against B. cinerea after 10 days than that of the yeast used alone, even if used at the standard rate ($10^7$ cfu/ml).

The composition of the invention which comprises $10^5$ cfu/ml of strain O and GU 0.001% w/v also offers a protection which is impressively better than the one provided by any composition of the state of the art which does not comprise GA or GU.

The latter composition according to the invention makes it possible to obtain total protection after 10 days and still 90% of protection after 14 days.

In a third series of experiments on apples, it has been shown that, according to the invention, compositions containing GA 0.01% w/v have a protective effect not only against B. cinerea but also against P. expansum.

It has also been found that a combination of strain O and GA 0.01% w/v have an enhanced efficacy over compositions of the state of the art after 7 days, not only against B. cinerea but also against P. expansum.

TABLE 3

| Strain O (cfu/ml) | GA (% w/v) | % protection against B. cinerea after 7 days | % protection against P. expansum After 7 days |
| --- | --- | --- | --- |
| $10^7$ | — | 95 | 79 |
| $10^5$ | — | 48 | 47 |
| — | 0.01 | 12 | 18 |
| $10^5$ | 0.01 | 77 | 73 |

The composition wherein strain O is used at the suboptimal rate of $10^5$ cfu/ml (hundred fold less than the standard rate) in combination with GA 0.01% w/v has, against each of the two pathogens, an enhanced efficacy compared to the use of strain O alone. Further, the comparison with the protective effects of GA 0.01% w/v used alone shows synergistic effects. As can be seen in table 3, the level of protection provided by this composition against P. expansum nearly reaches the one obtained by application of strain O at the normal rate.

In a fourth series of experiments, the stimulating effect of galacturonic acid (GA) on the antagonistic activity of C. oleophila strain O (used at the suboptimal rate of $10^5$ cfu/ml) has been compared to that of polygalacturonic acid (PGA) (table 4).

TABLE 4

| Strain O (cfu/ml) | GA (% w/v) | PGA (% w/v) | % protection against P. expansum after | | |
| --- | --- | --- | --- | --- | --- |
| | | | 6 days | 8 days | 10 days |
| $10^7$ | — | — | 71 | 59 | 37 |
| $10^5$ | — | — | 66 | 27 | 19 |
| — | 0.001 | — | 15 | 9 | 7 |
| — | — | 0.001 | 19 | 12 | 10 |
| $10^5$ | 0.001 | — | 87 | 62 | 43 |
| $10^5$ | — | 0.001 | 55 | 36 | 24 |

This experiment illustrates that the stimulation of antagonistic activity of strain O was obtained with galacturonic acid while this stimulating effect was not observed with polygalacturonic acid at the rate of 0.001%.

In a fifth series of experiments on apples, 2% w/v calcium chloride dihydrate ($CaCl_{20.2}H_2O$, Merck) has been added to some compositions according to the invention. Exceptionally good results have been obtained in the protection of apples against B. cinerea.

Indeed, a composition comprising $10^5$ cfu/ml of strain O, galacturonic acid monohydrate (GA) 0.001% w/v and $CaCl_{20.2}H_2O$ 2% w/v leads to a total protection (100%) up to 14 days, which is quite remarkable.

Example 2

Example 2 illustrates the fact that good protective effect may be also obtained by using compositions of the invention comprising stimulating agents consisting of uronic acids and antagonistic yeast's active against postharvest diseases caused by moulds on fruits of Pyrus species.

Vegetal Material

Pears (Pyrus communis L.cv. Conference) were harvested from untreated orchards in the 6 weeks preceding harvest in Melveren (Belgium) and stored in an Ultra low storage at 1±1° C. for 2 months before use.

Pathogen

B. cinerea (grey mould) strain was initially isolated from strawberries in Gembloux.

Pathogenic strain was stored on PDA covered by paraffin oil in tubes at 25° C. Starting from this stored material, the fungal strain was transferred to PDA at 25° C. Conidial suspension were prepared in an aqueous sterile solution of Tween 20 (0.05%), and was adjusted to the required concentration ($10^6$ spores/ml for B. cinerea) using a Bürker cell. Inoculation of the pathogen was performed using a spraying table at constant pressure (2 bars) until good cover of the fruits.

Antagonistic Micro-Organisms

The antagonistic yeast strains P. anomala "strain K" and C. oleophila "strain O" were produced in bioreactors. After centrifugation, the resulting paste was dried by lyophilization in the case of strain K and used as such for strain O. Both productions were rehydrated in peptone water (5 g/l NaCl, 1 g/l peptone and 0.5 ml/l Tween 20) 1 hour before application before diluting with water to the required concentration.

Treatment

Fruits were wounded using 1 mm deep and 1 mm diameter nails (4 wounds located on the equatorial line of the fruits) prior to application. Fruits were dipped in water (control), in the yeast suspensions at the required concentration during 2 minutes or in the standard Sumico WP (25,5% carbendazime+25,5% diethofencarb) from Aventis CropScience at 1 g/l during 30 seconds and then left at 20-25° C. before inoculation with the pathogens 24 hours later. Sumico WP is a commercially available fungicide having received a marketing authorisation in Belgium for postharvest treatment of apples and pears. After inoculation, fruits were stored in humidified plastic cages in dark conditions (25° C. and 90% RH).

TABLE 5

| Strain K (cfu/ml) | Sumico (g/l) | GU (% w/v) | $CaCl_2$ (% w/v) | % protection against B. cinerea after 15 days |
| --- | --- | --- | --- | --- |
| $10^7$ | — | — | | 34 |
| $10^8$ | — | — | | 25 |

TABLE 5-continued

| Strain K (cfu/ml) | Sumico (g/l) | GU (% w/v) | CaCl$_2$ (% w/v) | % protection against B. cinerea after 15 days |
|---|---|---|---|---|
| 10$^8$ | — | — | 2 | 66 |
| 10$^8$ | — | 0.001 | 2 | 76 |
| — | 1 | — | — | 88 |

It was surprisingly found that the use of GU at the rate of 0.001% w/v was stimulating the antagonistic activity of yeast's not only on apple fruits as shown in example 1, but also on pear fruits.

Moreover, the addition of GU 0.001% w/v to P. anomala strain K (at 10$^5$ cfu/ml instead of the standard rate of 10$^7$ cfu/ml) and 2% w/v calcium chloride dihydrate lead to a protection level closer to that obtained with the standard Sumico at the recommended rate against the grey mould on pears 15 days after treatment (table 5).

As can be seen in table 6, the addition of GA or GU at the rate of 0.001% to C. oleophila strain O (at 10$^5$ cfu/ml) and 2% w/v calcium chloride dihydrate have the effect of increasing the protection percentage to a level similar or even higher than that of the chemical standard against the grey mould on pears 9 days after treatment.

TABLE 6

| Strain O (cfu/ml) | Sumico (g/l) | GA (% w/v) | GU (% w/v) | CaCl$_2$ (% w/v) | % protection against B. cinerea after 9 days |
|---|---|---|---|---|---|
| 10$^7$ | — | — | — | — | 60 |
| 10$^6$ | — | — | — | — | 30 |
| 10$^6$ | — | — | — | 2 | 69 |
| 10$^6$ | — | 0.001 | — | 2 | 74 |
| 10$^6$ | — | — | 0.001 | 2 | 91 |
| 10$^7$ | — | 0.001 | — | 2 | 84 |
| — | 1 | — | — | — | 70 |

The effect of C. oleophila strain O at 10$^6$ cfu/ml together with GU at the rate of 0.001% is significantly higher than the one obtained with the standard Sumico at the recommended rate.

Example 3

Example 3 illustrates the fact that good protective effect may be also obtained by using compositions of the invention comprising stimulating agents consisting of uronic acids and antagonistic yeast's active against postharvest diseases caused by moulds on fruits of a third species, namely Citrus species.

Vegetal Material

Oranges (Citrus sinensis (L.) Ohl. cv. Valencia) were bought from wholesale dealers and stored in a cold room at 4±1° C. for maximum 15 days before use.

Pathogen

Penicillium digitatum strain CBS31948 (green mould of oranges) was obtained from the CentraalBureau Schimmelcultures, Netherlands collection and initially isolated from Citrus fruits. Conidia from the pathogenic strain were put in suspension in a glycerol solution (25%) and stored at −70° C. Starting from this stored material, the fungal strain was transferred to oat medium at 25° C. Conidial suspensions were prepared in an aqueous sterile solution of Tween 20 (0.05%). Before use, suspensions have been adjusted to the required concentration (10$^5$ spores/ml) using a Barker cell.

Antagonistic Microorganisms

The antagonistic yeast strain P. anomala "strain K" was obtained as in example 1. C. oleophila strain I-182 commercialised under the name Aspire™ was obtained from Ecogen Inc. Both microorganisms were subcultured as in example 1.

Treatment

Fruits were disinfected and wounded as in example 1. The wounds were treated by application of 20 pi of the compositions and inoculated after one hour with 20 pi of the pathogen conidial suspension. The percentage of protection is calculated as in example 1.

TABLE 7

| Strain K | GA | % protection against P. digitatum after | |
|---|---|---|---|
| (cfu/ml) | (% w/v) | 7 days | 10 days |
| 10$^8$ | — | 92 | 67 |
| 10$^7$ | — | 74 | 45 |
| — | 0.01 | 58 | 36 |
| 10$^7$ | 0.01 | 84 | 70 |

It is surprisingly found that the use of GA 0.01% w/v is efficient against postharvest disease not only on apple fruits but also on a Citrus species.

Moreover, the addition of GA 0.01% w/v allows to use a ten fold lower concentration of P. anomala strain K (10$^7$ instead of 10$^8$ cfu/ml) on oranges while keeping a protective level activity against the green mould of oranges cv Valencia up to 10 days after treatment (table 7).

As can be seen in table 8, the addition of GA at the rate of 0.01% allows to use a ten fold lower concentration (10$^7$ instead of 10$^8$ cfu/ml) of 1-182 (Aspire™) strain on oranges while keeping a similar protective level against the green mould of oranges cv Valencia 12 days after treatment.

TABLE 8

| Strain I-182 | GA | % protection against P. digitatum after | |
|---|---|---|---|
| (cfu/ml) | (% w/v) | 7 days | 12 days |
| 10$^8$ | — | 34 | 18 |
| 10$^7$ | — | 26 | 15 |
| 10$^7$ | 0.01 | 30 | 19 |

These experiments show that the addition of GA can lead to interesting complementations in protective activity for a variety of antagonistic yeast strains on Citrus fruits.

Example 4

Example 4 illustrates the fact that good protective effect may also be obtained by using compositions of the invention comprising stimulating agents consisting of uronic acids in combination with antagonistic fungi active against mould diseases on leaves of strawberry, grapevine and tomato.

Vegetal Material

Healthy green leaflets were harvested from 4 week old greenhouse plants of strawberry (cv. Elsenta), grapevine (cv. Müller Thurgau) and tomato (cv. Raïssa) grown at 25° C. with a photoperiod of 16 hours. Leaflets were then sterilized using gamma rays, dried at room temperature under sterile atmosphere for three weeks and stored in sealed plastic bags. They were rehydrated with sterile water overnight and washed thoroughly to remove soluble nutrients before use in the bioassays. Pathogen and antagonistic micro-organisms The pathogen *B. cinerea* strain 700 and the antagonistic micro-organism strain 385 of *U. atrum* were obtained from Plant Research International, formerly Research Institute for Plant Protection (Wageningen) (IPO-DLO) and initially isolated from a gerbera flower and the tip of an onion leaf respectively. The strain hereinafter designated as "strain 385" corresponds to strain 700.95 deposited as the CBS, Centraalbureau voor Schimmelcultures, as indicated above. The antagonistic strains of *U. atrum* 18558 and 18559 were obtained from the BBCM™/MUCL (Mycothèque Universitaire Catholique de Louvain). The fungal strains were grown on oat medium at 20° C. for 14 days. Conidial suspensions were prepared in an aqueous sterile solution of Tween 80 (0.01%), and were adjusted to the required concentrations using a Bürker cell.

Treatment

Healthy dead leaves of strawberry, tomato and grapevine were sprayed with *B. cinerea* ($10^4$ spores/ml or sp/ml) alone or simultaneously with *U. atrum* strains. Four rates of *U. atrum* were used: the standard rate of $2.10^8$ sp/ml, and the rates of $4.10^5$, $10^5$ and $2.10^4$ sp/ml, with or without galacturonic acid monohydrate (GA).

Four washed leaflets were placed on 0.75% water agar (w/v) in a Petri dish and sprayed with *B. cinerea* (5 µl/cm$^2$). Conidia of the antagonist *U. atrum* were also applied by spray just after the inoculation with the pathogen.

After 6 days incubation at 20° C. under a daily light exposition of 16 hours, *B. cinerea* spore coverage was evaluated on the three leaf substrates. The proportion of leaf area covered with conidiophores of *B. cinerea* (ranging from >0 to 100% at intervals of 10%) was evaluated by optical microscopy for each plant leaflet.

The lower the percentage of *B. cinerea* spore coverage, the better the protective activity of the composition.

In a first series of experiments, results of which are given in table 9, the evaluation of the protective activity of *U. atrum* strain 385 was carried out on three different vegetal materials.

TABLE 9

| *U. atrum* strain 385 | GA | % *B. cinerea* spore coverage after 6 days on | | |
|---|---|---|---|---|
| sp/ml | (% w/v) | Strawberry | Tomato | Grapevine |
| — | — | 99 | 91 | 94 |
| $2 \cdot 10^6$ | — | 16 | 7 | 27 |
| $4 \cdot 10^5$ | — | 14 | 17 | 60 |
| $10^5$ | — | 38 | 44 | 77 |
| $2 \cdot 10^6$ | 0.01 | 7 | 1 | 19 |
| $4 \cdot 10^5$ | 0.01 | 5 | 3 | 26 |
| $10^5$ | 0.01 | 14 | 34 | 66 |

Whatever the leaf substrate (strawberry, tomato, grapevine), the in situ assays showed that the composition containing GA 0.01% w/v stimulated the reduction of *B. cinerea* sporulation after 6 days of colonization when *U. atrum* 385 was applied at 4.105 sp/ml. The results were equivalent to or better than the protective level observed with the application of *U. atrum* 385 alone at 2.106 sp/ml.

The addition of GA allows to use a five fold lower rate of *U. atrum* strain 385 spores ($4.10^5$ instead of $2.10^6$ sp/ml) on tomato and grapevine without any significant reduction of protective level. This rate can be reduced up to 20 times ($10^5$ sp/ml) on strawberry, while keeping good results.

In a second series of experiments, the evaluation of the protective activity of compositions including *U. atrum* and GA was carried out with three *U. atrum* strains (Table 10).

TABLE 10

| Treatment | | | | |
|---|---|---|---|---|
| *U. atrum* 385 (sp/ml) | *U. atrum* 18558 (sp/ml) | *U. atrum* 18559 (sp/ml) | GA (% w/v) | % *B. cinerea* spore coverage on strawberry leaflets |
| — | — | — | — | 100 |
| $2 \cdot 10^6$ | — | — | — | 13 |
| $2 \cdot 10^6$ | — | — | 0.01 | 7 |
| — | $2 \cdot 10^6$ | — | — | 52 |
| — | $2 \cdot 10^6$ | — | 0.01 | 20 |
| — | — | $2 \cdot 10^6$ | — | 42 |
| — | — | $2 \cdot 10^6$ | 0.01 | 7 |

Compositions of the invention containing any of the 3 strains and GA 0.01% w/v showed an enhanced protective effect.

In a third series of experiments, the protective activity of a composition including *U. atrum* and GA was evaluated using different rates of GA (Table 11).

TABLE 11

| Treatment | | % *B. cinerea* spore coverage after 6 days | | |
|---|---|---|---|---|
| *U. atrum* 385 (sp/ml) | GA (% w/v) | Strawberry | Tomato | Grapevine |
| — | — | 97 | 90 | 92 |
| $2\ 10^6$ | — | 12 | 1 | 25 |
| $2\ 10^5$ | — | 25 | 10 | 38 |
| $2\ 10^5$ | 0.001 | 13 | 3 | 30 |
| $2\ 10^5$ | 0.01 | 12 | 12 | 32 |
| $2\ 10^5$ | 0.1 | 28 | 17 | 38 |

On strawberry leaflets, the application of compositions of the invention containing respectively GA 0.001% w/v and 0.01% w/v and *U. atrum* 385 at the suboptimal rate of $2\ 10^5$ sp/ml allowed to reach a protection level similar to that obtained with the antagonistic strain used alone at the standard rate of $2\ 10^6$ sp/ml.

On tomato leaflets, an equivalent reduction of *B. cinerea* sporulation to that provided by *U. atrum* 385 used alone (at $2\ 10^6$ sp/ml) was obtained in the composition of the invention containing *U. atrum* 385 ($2\ 10^5$ sp/ml) with GA 0.001% w/v.

On grapevine leaflets, the compositions of the invention containing GA 0.001% w/v also gave the best results to enable the stimulation of *U. atrum* antagonistic activity, although the level of protection was slightly less than that obtained through the use of *U. atrum* alone at the standard rate ($2\ 10^6$ sp/ml).

The optimal rate of galacturonic acid in compositions of the invention has thus to be adapted depending on the crop to be treated.

Example 5

Example 5 illustrates the fact that good protective effect may be obtained by using compositions according to the invention and stimulating agents consisting of polysaccharides derived from glucans and mannans and mixtures thereof and antagonistic yeast's active against postharvest diseases caused by moulds on fruits of *Malus* species.

In particular, compositions of the invention containing either an antagonistic microorganism and one stimulating agent consisting of polysaccharides or an antagonistic micro-organism and two stimulating agents also proved efficient.

Vegetal material, pathogens, antagonistic micro-organisms and treatment method were as in example 1. The wounds were treated by application of 50 pi of compositions of the state of the art or compositions of the invention. The effect of the compositions against postharvest apple rots caused by *B. cinerea* has been evaluated under controlled conditions.

The following products were used
M, which stands for mannans (Sigma M7504)
YGT, which stands for 70-80% w/v beta-1,3-glucans from Ohly DHW Deutsche Hefwerke GmbH & Co KG,
HCT, which stands for a product containing 25% w/v beta-1,3-glucans and 23% w/v mannans, equally from Ohly DHW Deutsche Hefwerke GmbH & Co KG.

In a first series of experiments, standard compositions of strain K have been used as control.

TABLE 12

| Strain K (cfu/ml) | M (mannans) (% w/v) | YGT (beta-1,3-glucans) (% w/v) | HCT (beta-1,3-glucans + mannans) (% w/v) | % protection against *B. cinerea* after | | | |
|---|---|---|---|---|---|---|---|
| | | | | 7 days | 10 days | 14 days | 20 days |
| $10^7$ | — | — | — | 100 | 97 | 79 | 48 |
| $10^5$ | — | — | — | 88 | 79 | 64 | 21 |
| — | 0.02 | — | — | 100 | 78 | 55 | 16 |
| — | 0.2 | — | — | 100 | 93 | 68 | 26 |
| — | — | — | 0.02 | 100 | 81 | 63 | 23 |
| — | — | — | 0.2 | 97 | 88 | 63 | 37 |
| — | — | 0.02 | — | 45 | 19 | 9 | 0 |
| — | — | 0.2 | — | 46 | 23 | 26 | 0 |
| $10^5$ | 0.02 | — | — | 100 | 100 | 99 | 61 |
| $10^5$ | 0.2 | — | — | 100 | 100 | 93 | 57 |
| $10^5$ | — | — | 0.2 | 100 | 95 | 83 | 37 |
| $10^5$ | — | 0.02 | — | 98 | 91 | 79 | 35 |
| $10^5$ | — | 0.2 | — | 100 | 98 | 84 | 40 |

According to the invention, it has surprisingly been found that M, YGT and HCT are stimulating agents which have an effect on the protection against *B. cinerea*.

Compositions of the invention containing strain K (at $10^5$ cfu/ml) and mannans (at 0.02% w/v or 0.2% w/v) allow to obtain a total protection against *B. cinerea* after 10 days.

Even after 14 days, the level of protection is extremely high (99 and 93% respectively) and far better than the result obtained with the application of strain K alone at the normal rate. The protective activity obtained after 20 days is also enhanced.

Compositions of the invention containing strain K at $10^5$ cfu/ml and beta-1,3-glucans (YGT) also give results indicating an enhanced protective activity as compared with the use of strain K alone.

The protective activity of a composition of the invention containing a mixture of mannans and beta-α-1,3-glucans (HCT) at 0.2% w/v and strain K at $10^5$ cfu/ml after 14 days is superior to the one provided by strain K at $10^7$ cfu/ml.

In second series of experiments, results of which are given in table 13, standard compositions of the state of the art containing strain O have been used as control.

TABLE 13

| Strain O (cfu/ml) | M (% w/v) | YGT (% w/v) | HCT (% w/v) | GA (% w/v) | % protection against *B. cinerea* after | | | |
|---|---|---|---|---|---|---|---|---|
| | | | | | 7 days | 10 days | 14 days | 20 days |
| $10^7$ | — | — | — | — | 100 | 100 | 93 | 64 |
| $10^5$ | — | — | — | — | 91 | 60 | 30 | 0 |
| — | 0.02 | — | — | — | 100 | 78 | 55 | 16 |
| — | 0.2 | — | — | — | 100 | 93 | 68 | 28 |
| — | — | — | 0.02 | — | 100 | 81 | 63 | 23 |
| — | — | — | 0.2 | — | 97 | 88 | 63 | 37 |
| — | — | 0.02 | — | — | 45 | 19 | 9 | 0 |
| — | — | 0.2 | — | — | 46 | 23 | 26 | 0 |
| — | — | — | — | 0.001 | 87 | 47 | 33 | 0 |
| $10^5$ | 0.02 | — | — | — | 96 | 88 | 82 | 44 |
| $10^5$ | 0.2 | — | — | — | 97 | 89 | 81 | 58 |
| $10^5$ | — | — | 0.2 | — | 95 | 87 | 67 | 37 |
| $10^5$ | — | 0.02 | — | — | 94 | 86 | 72 | 33 |
| $10^5$ | — | 0.2 | — | — | 91 | 83 | 57 | 20 |
| $10^5$ | — | — | 0.2 | 0.001 | 100 | 88 | 75 | 70 |

Results obtained with strain O at $10^5$ cfu/ml are not satisfactory. The protective activity against the pathogen after 20 days is even absolutely absent.

The application of compositions of the invention containing $10^5$ cfu/ml of strain O and mannans M (0.02% and 0.2% w/v respectively) shows enhanced protective activity as compared to the use of strain O alone at this suboptimal rate. Similar results were obtained with the compositions of the invention containing beta-1,3-glucans (YGT) or a mixture of mannans and beta-1,3-glucans (HCT).

The last composition of the invention illustrated in table 13 contains strain O at $10^5$ cfu/ml as well as both a mixture of mannans and beta-1,3-glucans (HCT) and galacturonic acid monohydrate (GA) 0.001% w/v. The level of protection obtained after 20 days appears to be particularly high.

In a third series of experiments, 2% w/v calcium chloride dihydrate ($CaCl_{2`.2}H_2O$, Merck) has been added to some compositions of the invention. Very good results have been obtained in the protection of apples against *B. cinerea*. Indeed, a composition comprising $10^5$ cfu/ml of strain O, mannans M 0.02% w/v leads to a protection of 90% up to 14 days.

In a fourth series of experiments, results of which are given in table 14, it has been shown that compositions of the invention containing a combination of strain K and 0.2% w/v HCT or 0.2% w/v YGT have an improved efficacy after 7 days over strain K used alone, not only against *B. cinerea*, but also against *P. expansum*.

TABLE 14

| Strain K (cfu/ml) | HCT % w/v | YGT % w/v | % protection against *B. cinerea* After 7 days | % protection against *P. expansum* after 7 days |
|---|---|---|---|---|
| $10^7$ | — | — | 92 | 90 |
| $10^5$ | — | — | 66 | 77 |
| $10^5$ | 0.2 | — | 79 | 83 |
| $10^5$ | — | 0.2 | 87 | 65 |

In a fifth series of experiments, results of which are given in table 15, compositions of the invention containing a combination of strain O and 0.2% w/v HCT or YCT also showed enhanced efficacy after 7 days over the use of strain O alone, not only against *B. cinerea*, but also against *P. expansum*.

TABLE 15

| Strain O (cfu/ml) | HCT % w/v | YGT % w/v | % protection against *B. cinerea* after 7 days | % protection against *P. expansum* after 7 days |
|---|---|---|---|---|
| $10^7$ | — | — | 95 | 79 |
| $10^5$ | — | — | 48 | 34 |
| $10^5$ | 0.2 | — | 85 | 90 |
| $10^5$ | — | 0.2 | 74 | 93 |

It is particularly surprising that compositions of the invention containing strain O at $10^5$ cfu/ml and 0.2% w/v HCT or YGT are even more efficient against *P. expansum* after 7 days than compositions of the state of the art containing a hundred fold higher rate of the strain.

Example 6

Example 6 illustrates the enhanced protective effect of compositions of the invention comprising stimulating agents consisting of mannans and beta-1,3-glucans and mixtures thereof and antagonistic yeast's active against postharvest diseases caused by moulds on fruits of *Citrus* species.

Vegetal material, pathogens, antagonistic agents and treatment method were as in example 3. The wounds were treated by application of 20 pl of compositions of the state of the art or compositions of the invention. The effect of the compositions against postharvest rots caused by *P. digitatum* has been evaluated under controlled conditions.

In a first series of experiments, results of which are given in table 16, the efficacy of a composition of the invention containing $10^7$ cfu/ml of strain K and a mixture of mannans and beta-1,3-glucans proved as efficient against *P. digitatum* after 10 days as strain K applied at a ten times higher rate.

TABLE 16

| Strain K (cfu/ml) | YGT (% w/v) | % protection against *P. digitatum* after | |
|---|---|---|---|
| | | 7 days | 10 days |
| $10^8$ | — | 92 | 67 |
| $10^7$ | — | 74 | 45 |
| $10^7$ | 0.2 | 83 | 68 |

In a second series of experiments (table 17), it has been shown that compositions of the invention containing $10^7$ cfu/ml of strain I-182 commercialised under the name Aspire™ and 0.2% w/v YGT has a drastically improved efficacy.

TABLE 17

| Strain I-182 (cfu/ml) | YGT (% w/v) | % protection against *P. digitatum* after | |
|---|---|---|---|
| | | 7 days | 12 days |
| $10^8$ | — | 34 | 18 |
| $10^7$ | — | 26 | 15 |
| $10^7$ | 0.2 | 70 | 31 |

Indeed, said composition has a protective activity against *P. digitatum* after 7 days which is two times greater than the one of a composition of the state of the art containing ten fold the rate of the yeast.

CONCLUSIONS

All the results given in the examples show that the compositions of the invention present a longer stability in time and/or a higher efficiency than that provided by compositions of the state of the art containing micro-organisms strains used at the same application rate.

The stimulating agents of the present invention allow lowering the concentration of an antagonistic micro-organism without lowering the efficiency of the compositions against pathogens. They also allow lowering the concentration of an antagonistic micro-organism while prolonging the duration of the efficiency of the composition against pathogens.

What is claimed is:

1. A composition suitable for use against one or more pathogens, comprising at least one antagonistic micro-organism and at least one stimulating agent selected from the group consisting of uronic acid monomers, mannans, salts and hydrates thereof or mixtures of said agents, wherein said at least one antagonistic micro-organism is selected from the group consisting of *U. atrum, Pichia anomala* and *Candida oleophila*.

2. The composition according to claim 1, which further comprises a beta-1,3-glucan.

3. The composition according to claim 1, wherein the amount of the at least one stimulating agent is at a concentration between 0.001 and 0.2% w/v.

4. The composition according to claim 1, wherein the antagonistic microorganism is a strain selected from the group consisting of *Pichia anomala*(Hansen) Kurtzman strain K , *Candida oleophila* Montrocher strain O, and *Candidaoleophila* Montrocher commercial strain I-182.

5. The composition according to claim 1, wherein said antagonistic micro-organism is present at a concentration ranging from $10^5$ to $10^8$ cfu/ml.

6. The composition according to claim 1, wherein the one or more pathogens are selected from the group consisting of *Botrytis cinerea, Penicillium expansum, P. digitatum, P. italicum,* and *Rhizopus* spp.

7. The composition according to claim 1, which further comprises at least one salt selected from the group consisting of calcium salt, sodium salt, and potassium salt.

8. The composition according to claim 7, wherein the calcium salt is selected from the group consisting of calcium chloride, calcium bicarbonate and calcium propionate.

9. The composition according to claim 8, wherein the amount of salt is in the range of 0.01% to 2% w/v.

10. A method for the biocontrol of diseases caused pathogens selected from the group consisting of *Botrytis cinerea, Penicillium expansum, P. digitatum, P. italicum,* and *Rhizopus* spp, to vegetal material selected from the group consisting of *Malus* spp., *Pyrus* spp., *Citrus* spp., tomato, grapevine and strawberry, comprising the step of applying a composition according to claim 1 to said vegetal material.

\* \* \* \* \*

UNITED STATES PATENT AND TRADEMARK OFFICE
CERTIFICATE OF CORRECTION

PATENT NO. : 7,241,439 B2
APPLICATION NO. : 10/471144
DATED : July 10, 2007
INVENTOR(S) : Jijakli et al.

It is certified that error appears in the above-identified patent and that said Letters Patent is hereby corrected as shown below:

Column 1, Line 55, "Applied Microbiolgy group," should be changed to --Applied Microbiology group,--

Column 3, Line 52, "Place Croix Du sud 2-bte. 6, B1348Louvain-la-Newve," should be changed to --Place Croix du Sud 2-bte. 6, B1348, Louvain-la-Neuve,--

Column 4, Line 51, "(*Malus domestics*" should be changed to --(*Malus domestica*--

Column 5, Line 3, "using a Bärker cell." should be changed to --using a Bürker cell.--

Column 5, Line 40, "After a 24 h at" should be changed to --After a 24h at--

Column 8, Line 2, "($CaCl_{20.2}H_2O$, Merck)" should be changed to --($CaCl_2.2H_2O$, Merck)--

Column 8, Line 8, "$CaCl_{20.2}H_2O$2% w/v leads" should be changed to --$CaCl_2.2H_2O$ 2% w/v leads--

Column 8, Line 66, "$10^8$" should be changed to --$10^6$--

Column 9, Line 6, "$10^8$" should be changed to --$10^6$--

Column 9, Line 7, "$10^8$" should be changed to --$10^6$--

Column 9, Line 15, "(at $10^5$ cfu/ml" should be changed to --(at $10^6$ cfu/ml--

Column 9, Line 21, "(at $10^5$ cfu/ml)" should be changed to --(at $10^6$ cfu/ml)--

Column 9, Line 67, "using a Barker cell." should be changed to --using a Bürker cell.--

Column 10, Line 10, "of 20 pi of the" should be changed to --of 20 µl of the--

Column 10, Line 11, "with 20 pi of the" should be changed to --with 20 µl of the--

UNITED STATES PATENT AND TRADEMARK OFFICE
CERTIFICATE OF CORRECTION

PATENT NO.       : 7,241,439 B2
APPLICATION NO.  : 10/471144
DATED            : July 10, 2007
INVENTOR(S)      : Jijakli et al.

It is certified that error appears in the above-identified patent and that said Letters Patent is hereby corrected as shown below:

Column 11, Line 2-3, "Pathogen and antagonistic micro-organisms The pathogen" should be changed to --Pathogen and Antagonistic Micro-Organisms (heading) The pathogen--

Column 11, Line 23, "rate of $2.10^8$ sp/ml," should be changed to --rate of $2.10^6$ sp/ml,--

Column 13, Line 13, "products were used" should be changed to --products were used:--

Column 13, Line 65, "In second series" should be changed to --In a second series--

Column 15, Line 38, "($CaCl_{20.2}H_2O$, Merck)" should be changed to --($CaCl_2.2H_2O$, Merck)--

Column 16, Line 47, "of 20 pl of compositions" should be changed to --of 20 µl of compositions--

Column 18, Line 12, "strain K , *Candida*" should be changed to --strain K, *Candida*--

Signed and Sealed this

Fourth Day of December, 2007

JON W. DUDAS
*Director of the United States Patent and Trademark Office*